US008115023B2

(12) United States Patent
Petasis

(10) Patent No.: US 8,115,023 B2
(45) Date of Patent: Feb. 14, 2012

(54) BENZO LIPOXIN ANALOGUES

(75) Inventor: Nicos A. Petasis, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/711,051

(22) Filed: Feb. 23, 2010

(65) Prior Publication Data

US 2010/0152290 A1 Jun. 17, 2010

Related U.S. Application Data

(63) Continuation of application No. 11/398,481, filed on Apr. 4, 2006, now Pat. No. 7,683,193, which is a continuation of application No. 10/938,729, filed on Sep. 10, 2004, now abandoned.

(60) Provisional application No. 60/502,094, filed on Sep. 10, 2003.

(51) Int. Cl.
*C07C 59/00* (2006.01)
(52) U.S. Cl. ......... 554/218; 514/473; 514/532; 514/559
(58) Field of Classification Search .................. 514/473, 514/532, 559; 554/218
See application file for complete search history.

(56) References Cited

U.S. PATENT DOCUMENTS

| | | | |
|---|---|---|---|
| 3,710,795 | A | 1/1973 | Higuchi et al. |
| RE28,819 | E | 5/1976 | Thomspson |
| 4,252,951 | A | 2/1981 | Jackson et al. |
| 4,328,245 | A | 5/1982 | Yu et al. |
| 4,358,603 | A | 11/1982 | Yu |
| 4,409,239 | A | 10/1983 | Yu |
| 4,410,545 | A | 10/1983 | Yu et al. |
| 4,522,811 | A | 6/1985 | Eppstein et al. |
| 5,033,252 | A | 7/1991 | Carter |
| 5,052,558 | A | 10/1991 | Carter |
| 5,323,907 | A | 6/1994 | Kalvelage |
| 2005/0203184 | A1 | 9/2005 | Petasis |
| 2006/0270734 | A1 | 11/2006 | Petasis |

FOREIGN PATENT DOCUMENTS

| | | | |
|---|---|---|---|
| JP | 03-227922 | | 8/1991 |
| WO | 0170664 | * | 9/2001 |
| WO | WO 01/70664 | | 9/2001 |

OTHER PUBLICATIONS

JAPIO Abstr. of JP-03/227922, 1991.
Alpdogan Kantarci et al., "Lipoxin signaling in neutrophils and their role in periodontal disease", Prostaglandins, Leukotrienes and Essential Fatty Acids 73 (2005), pp. 289-299.
Amiran Ariel et al., "Aspirin-Triggered Lipoxin $A_4$ and $B_4$ Analogs Block Extracellular Signal-Regulated Kinase-Dependent TNF-α Secretion from Human T Cells", The Journal of Immunology, 2003, 170, pp. 6266-6272.
Andrew T. Gewirtz et al., "Lipoxin $A_4$ Analogs Attenuate Induction of Intestinal Epithelial Proinflammatory Gene Expression and Redue the Severity of Dextran Sodium Sulfate-Induced Colitis", The Journal of Immunology, 2002, 168, pp. 5260-5267.
Ansel, H.C, *Introduction to Pharmaceutical Dosage Forms*, Fourth Edition, Philadelphia: Lea & Febiger, p. 126 (1985).
Arndt J. Schottelius et al., "An Aspirin-Triggered Lipoxin $A_4$ Stable Analog Displays a Unique Topical Anti-Inflammatory Profile", The Journal of Immunology, 2002, 169, pp. 7063-7070.
B. D. Levy, "Lipoxins and lipoxin analogs in asthma", Prostaglandins, Leukotrienes and Essential Fatty Acids 73 (2005), pp. 231-237.
Banker, G.S. et al., Modern Pharmaceutics, $3^{rd}$ ed. Marcel Dekker, New York, 1996, p. 596.
Braga et al., "Making crystals from crystals: a green route to crystal engineering and polymorphism," ChemComm 2005, 3635-3645.
Bruce D. Levy et al., "Dimished Lipoxin Biosysthesis in Sever Asthma", American Journal of Respiratory and Critical Care Medicine, vol. 172, 2005, pp. 824-830.
Bruce D. Levy et al., "Multi-pronged inhibition of airway hyperresponsiveness and inflammation by lipoxin $A_4$", Nature Medicine, vol. 8, No. 9, Sep. 2002, pp. 1018-1023.
Charles N. Serhan et al., "Reduced Inflammation and Tissue Damage in Transgenic Rabbits Overexpressing 15-Lipoxygenase and Endogenous Anti-inflammatory Lipid Mediators", The Journal of Immunology, 2003, 171, pp. 6856-6865.
Charles N. Serhan, "Lipoxins and aspirin-triggered 15-epi-lipoxin biosynthesis: an update and role in anti-inflammation and pro-resolution", Prostaglandins & Other Lipid Mediators, 68-69 (2002), pp. 433-455.
Charles N. Serhan, "Lipoxins and aspririn-triggered 15-epi-lipoxins are the first lipid mediators of endogenous anti-inflammation and resolution", Prostaglandins, Leukotrienes and Essential Fatty Acids 73 (2005), pp. 141-162.
Charles Serhan et al., Design of Lipoxin $A_4$ Stable Analogs that Block Transmigration and Adhesion of Human Neutrophils, Biochemistry, 1994, 34, pp. 14609-14615.
Charles Serhan et al., "Lipoxin $A_4$ Metabolism by Differentiated HL-60 Cells and Human Monocytes: Conversion to Novel 15-Oxo and Dihydro Products", Biochemistry, 1993, 32, pp. 6313-6319.
Charles Serhan, "Lipoxin biosynthesis and its impact in inflammatory and vascular events", Biochimica et Biophysica Acta 1212, 1994, pp. 1-25.
Christophe Dugave et al., "Cis-Trans Isomerization of Organic Molecules and Biomolecules: Implications and Applications", Chemical Reviews, 2003, 103, pp. 2475-2532.
Christopher L. Karp et al., "Cystic fibrosis and lipoxins", Prostaglandins, Leukotrienes and Essential Fatty Acids 73 (2005), pp. 263-270.
Christopher L. Karp et al., Defective lipoxin-mediated anti-inflammatory activity in the cystic fibrosis airway, Nature Immunology, Apr. 2004, vol. 5, No. 4, pp. 388-392.
Clary B. Clish et al., "Oxidoreductases in Lipoxin $A_4$ Matabolic Inactivation", The Journal of Biological Chemistry, vol. 275, No. 33, Issue of Aug. 18, 2000, pp. 25372-25380.
Cyclopedic Medical Dictionary, 16th Ed., C.W. Taber & C.L. Thomas (Eds.) F.A. Davis, Philadelphia, 1989, entry for "preventive" p. 1483.

(Continued)

Primary Examiner — Deborah D Carr
(74) Attorney, Agent, or Firm — Fish & Richardson P.C.

(57) ABSTRACT

Benzolipoxin analogs, methods of their preparation and pharmaceutical compositions containing the compounds are provided. The compounds and compositions are useful in methods for treatment of various diseases, including, inflammation, autoimmune disease and abnormal cell proliferation.

22 Claims, No Drawings

OTHER PUBLICATIONS

DiCarmo Oyama and Iuri Louro, "Multiple Sclerosis," Gale Encyclopedia of Neurological Disorders, Stacey Chamberlin and Brigham Narins, Eds., Detroit: Gale, 2005, vol. 2. p. 561.

Fierro, I.M., "Lipoxin A4 and aspirin-triggered 15-epi-lipoxin A4 inhibit human neutrophil migration: comparisons between synthetic 15 epimers in chemotaxis and transmigration with microvessel endothelial cells and epithelial cells.," J Immunol 170(5): 2688-2694 (Mar. 1, 2003).

Geraldine Canny et al., "Lipid mediator expression of bactericidal/permeability-increasing protein (BPI) in human mucosal epithelia", Proceeding of the National Academy of Sciences of the United States of America, 2002, 99, pp. 3902-3907.

Gerard Bannenberg et al., "Lipoxins and Novel 15-epi-lipoxin analogs display potent anti-inflammatory actions after oral administration", British Journal of Pharmacology, 2004, 143, pp. 43-52.

IUPAC-IUB Commission on Biochemical Nomenclature, "Abbreviated Nomenclature of Synthetic Polypeptides (Polymerized Amino Acids), Revised Recommendations (1971)," Biochemistry, 11:942-944 (1972).

Jason Goh et al., "Lipoxin $A_4$ and Aspirin-Triggered 15-Epi-Lipoxin $A_4$ Antagonize TNF-α-Stimulated Neutrophil-Enterocyte Interactions in Vitro and Attenuate TNF-α-Induced Chemokine Release and Colonocyte Apoptosis in Human Intestinal Mucosa Ex Vivo",The Journal of Immunology, 2001, 167, pp. 2772-2780.

John L. Wallace et al., Lipoxins in gastric mucosal health & disease, Prostaglandins, Leukotrienes and Essential Fatty Acids 73 (2005), pp. 251-255.

József, L., "Lipoxin A4 and aspirin-triggered 15-epi-lipoxin A4 inhibit peroxynitrite formation, NF-kappa B and AP-1 activation, and IL-8 gene expression in human leukocytes," Proc Natl Acad Sci USA 99(20):13266-13271 (Oct. 1, 2002).

Karsten Gronert, "Lipoxins in the eye and their role in wound healing", Prostaglandins, Leukotrienes and Essential Fatty Acids 73 (2005), pp. 221-229.

Maddox, J.F. et al., "Lipoxin A4 stable analogs are potent mimetics that stimulate human monocytes and THP-1 cells via a G-protein-linked lipoxin A4 receptor," J. Biol. Chem., 272(11): 6972-6978 (Mar. 1997).

McGraw-Hill Dictionary of Scientific and Technical Terms, Ed. Sybil P. Parker, Fifth Edition, New York: McGraw-Hill, 1994, p. 1601, entry for "psoriasis".

Melloni's Illustrated Medical Dictionary, 4th Ed., J.B. Melloni & I. Dox, (Eds.), Parthenon, New York, 2002 entry for "preventive", p. 528.

Merriam-Webster's Medical Desk Dictionary, Merriam-Webster: Springfield, 2002, entries for "inflammatory bowel disease" on p. 391, "systemic lupus erythematosus" on p. 811, "vasculitis" on p. 871.

Mosby's Medical, Nursing and Allied Health Dictionary, 4th Anderson et al. (Eds.), Mosby, St. Louis, MO, 1994, entry for "preventive", p. 1272.

Nan Chiang et al., "Anti-inflammatory circuitry: Lipoxin, aspirin-triggered lipoxins and their receptor ALX", Prostaglandins, Leukotrienes and Essential Fatty Acids 73 (2005), pp. 163-177.

Niamh E Kieran et al., Lipoxins: Potential anti-inflammatory, proresolution, and antifibrotic mediators in renal disease, Kidney International, vol. 65, 2004, pp. 1145-1154.

Nicolaou,, K.C., "Lipoxins and Related Eicosanoids: Biosynthesis, Biological Properties, and Chemical Synthesis," Angewandte Chemie International Edition 30(9): 1100-1116 (1991).

Nicos A. Petasis et al., "Design and synthesis of benxo-lipoxin $A_4$ analogs with enhanced stability and potent anti-inflammatory properties", Bioorganic & Medicinal Chemistry Letters 18, 2008, pp. 1382-1387.

Nicos A. Petasis et al., "Design, synthesis and bioactions of novel stable mimetics of lipoxins and aspirin-triggered lipoxins", Prostaglandins, Leukotrienes and Essential Fatty Acids 73 (2005), pp. 301-321.

Polsdorfer, J. Ricker, "Graft-vs.-host Disease," Gale Encyclopedia of Medicine, Jacqueline L. Longe (Ed.). vol. 3. 2nd ed. Detroit: Gale, 2002, p. 1481.

Robinson, R., "Polymyositis", The Gale Encyclopedia of Medicine, Jacqueline L. Longe. (Ed.), vol. 4. 2nd ed. Detroit: Gale, 2002, p. 2666.

S. Fiore et al., "Lipoxin $A_4$ biology in the human synovium. Role of the ALX signaling pathways in modulation of inflammatory arthritis", Prostaglandins, Leukotrienes Essential Fatty Acids, 2005, 73, pp. 189-196.

Samuelsson, B. et al., "Leukotrienes and lipoxins: structures, biosynthesis, and biological effects," Science 237(4819):1171-1176 (Sep. 4, 1987).

Scalia, R. et al., "Lipoxin A4 stable analogs inhibit leukocyte rolling and adherence in the rat mesenteric microvasculature: role of P-selectin," Proc. Nat. Acad. Sci. USA, 94: 9967-9972 (Sep. 2, 1997).

Serhan, C., "Lipoxins and novel aspirin-triggered 15-epi-lipoxins (ATL): a jungle of cell-cell interactions or a therapeutic opportunity?," Prostaglandins 53(2):107-137, (Feb. 1997).

Serhan, C.N. et al., "Lipoxins, aspirin-triggered 15-epi-lipoxin stable analogs and their receptors in anti-inflammation: a window for therapeutic opportunity," Chapter 8 in *Advances in Eicosanoid Research*, Ernst Schering Res Found Workshop, Serhan, C.N. and H.D. Perez (Eds.), Berlin: Springer-Verlag, (31):143-185 (2000).

Serhan, C.N., "Eicosanoids in leukocyte function," Current Opinion in Hematology 1(1): 69-77 (Jan. 1994).

Song Hong et al., "Novel Docosatrienes and 17S-Resolvins Generated from Docosahexaenoic Acid in Murine Brain, Human Blood, and Glial Cells", The Journal Biological Chemistry, Apr. 25, 2003, vol. 278, No. 17, 14677-14687.

Stefano Fiorucci et al., "A β-oxidation-resistant lipoxin $A_4$ analog treats hapten-induced colitis by attenuating inflammation and immune dysfunction", Proceeding of the National Academy of Sciences of the United States of America, Nov. 2, 2004, vol. 101, No. 44, 15736-15741.

The Dictionary of Modern Medicine, J.C. Segen, MD (Ed.), Park Ridge: Parthenon, 2002, entry for "Multiple Sclerosis" p. 471.

Tomoko Takano et al., "Aspirin-triggered 15-Epi-Lipoxin $A_4$ (LX $A_4$) Stable Analogues Are Potent Inhibitors of Acute Inflammation: Evidence for Anti-inflammatory Receptors", The Journal of Experimental Medicine, May 5, 1997, vol. 185, No. 9, pp. 1693-1704.

Tomoko Takano et al., Neutrophil-mediated Changes in Vascular Permeability are Inhibited by Topical Application of Aspirin-triggered 15-epi-lipoxin $A_4$ and Novel Lipoxin $B_4$ Stable Analgogues, The Journal of Clinical Investigation, Feb. 1998, vol. 101, No. 4, pp. 819-826.

William Guilford et al., "Novel 3-Oxa Lipoxin $A_4$ Analogues with Enhanced Chemical and Metabolic Stability Have Anti-inflammatory Activity in Vivo", Journal of Medical Chemistry, 2004, vol. 47, No. 8, pp. 2157-2164.

William Guilford et al., "Second-generation beta-oxidation resistant 3-oxa-lipoxin $A_4$ analogs", Prostaglandins, Leukotrienes and Essential Fatty Acids 73 (2005), pp. 245-250.

Wolff, Mandred E. Burger's Medicinal Chemistry, $5^{th}$ ed, Part 1, John Wiley & Sons, 1995, pp. 975-977.

* cited by examiner

BENZO LIPOXIN ANALOGUES

CROSS-REFERENCE TO RELATED APPLICATIONS

This application is a continuation application and claims the benefit of priority under 35 U.S.C. §120 of U.S. application Ser. No. 11/398,481, filed Apr. 4, 2006 now U.S. Pat. No. 7,683,193, which is a continuation of and claims the benefit of priority under 35 U.S.C. §120 of U.S. application Ser. No. 10/938,729, filed Sep. 10, 2004 now abandoned, which claims the benefit of priority under 35 U.S.C. §119(e) to U.S. provisional application Ser. No. 60/502,094, filed Sep. 10, 2003. The disclosure of each of the prior applications is considered part of and is incorporated by reference in the disclosure of this application.

FEDERALLY SPONSORED RESEARCH OR DEVELOPMENT

The invention was made with government support under Grant No. PO1-DE13499 awarded by the National Institutes of Health. The government has certain rights in the invention.

FIELD OF THE INVENTION

Compounds, compositions and methods using benzo lipoxin analogs for the prevention, amelioration and treatment of a variety of disorders, such as inflammatory diseases, autoimmune diseases and proliferative diseases.

BACKGROUND OF THE INVENTION

The lipoxins (LX) are tetraene-containing eicosanoids generated from arachidonic acid via several pathways involving the combined action of various lipoxygenases. (Science 1987, 237, 1171. Angew. Chem. Int. Ed. Engl. 1991, 30, 1100. Curr. Opin. Hematology 1994, 1, 69. Serhan, C. N. Biochim. Biophys. Acta 1994, 1212, 1. Prostaglandins & other Lipid Mediators 2002, 68-69, 433.). Two major structural types of LX have been identified, namely LXA4 and LXB4 (Scheme 1). The LX are generated largely transcellulary (e.g. via interactions between epithelial cells and neutrophils). Recent studies by Serhan have shown that, while acetylation of COX-1 by aspirin inhibits prostanoid formation, similar acetylation of COX-2 allows the formation of 15R-HETE, which is converted to 15-epi lipoxins (aspirin-triggered lipoxins) (Scheme 1). (Curr. Opin. Hematology 1994, 1, 69. Serhan, C. N. Biochim. Biophys. Acta 1994, 1212, 1. Prostaglandins & other Lipid Mediators 2002, 68-69, 433.).

Scheme 1

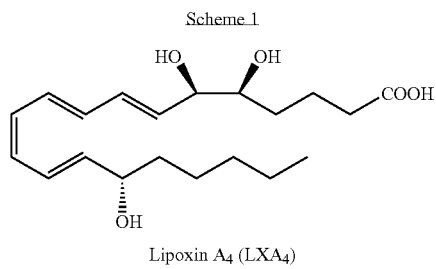

Lipoxin A4 (LXA4)

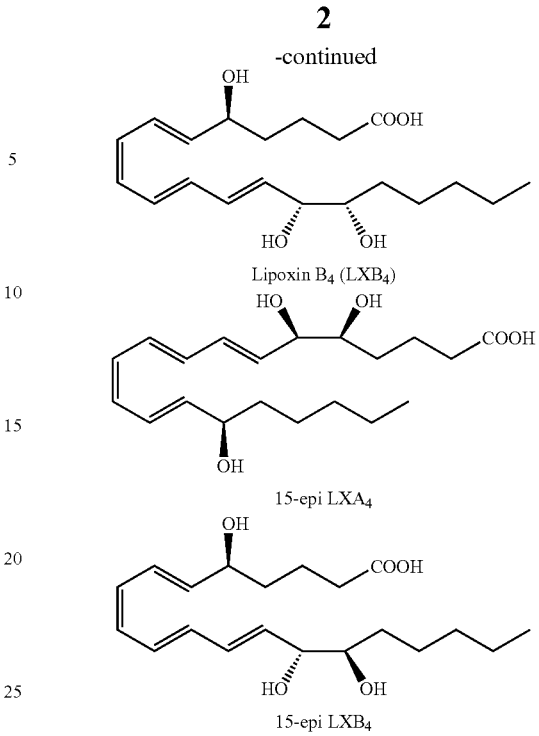

A key feature of LX that distinguishes them from most other eicosanoid mediators (or modulators) of inflammation is their potent antiinflammatory actions (Prostaglandins 53:107, 1997; Prostaglandins & other Lipid Mediators 68-69: 433, 2002). The in vitro and in vivo activities of the best-characterized lipoxin, LXA4, include: (a) inhibition of neutrophil chemotaxis, adherence, and transmigration; (b) suppression of neutrophil activation (including NF-kB activation, superoxide generation and elastase secretion); (c) suppression of IL-8 production by epithelia and leukocytes; (d) upregulation of bactericidal permeability-increasing protein expression in epithelial cells; (e) upregulation of monocyte chemotaxis; (f) upregulation of monocyte ingestion of apoptotic neutrophils (Prostaglandins 53:107, 1997; Prostaglandins & other Lipid Mediators 68-69:433, 2002; Proc Natl Acad Sci USA 99:13266, 2002; Proc Natl Acad Sci USA 99:3902, 2002). In a variety of in vivo models, LX have been shown to prevent neutrophil-mediated damage, and promote the resolution of neutrophil-mediated inflammation (Ernst Schering Res Found Workshop 31:143, 2000; Prostaglandins 53:107, 1997; Prostaglandins & other Lipid Mediators 68-69: 433, 2002). Notably, LX analogues have recently been shown to downmodulate allergic pulmonary inflammatory responses in mouse models (Biochemistry 1995, 34, 14609. J. Biol. Chem. 1997, 272, 6972. Proc. Nat. Acad. Sci. 1997, 94, 9967. Nature Immunol 8:1018, 2002. J Immunol 2003 170: 2688).

Several studies have established the facile metabolic deactivation of the lipoxins. As a result, in order to develop biostable analogs of LX, it is important to modify their structures in order to enhance their chemical and in vivo stability. Several biostable LX analogs have been reported. (Biochemistry 1995, 34, 14609).

SUMMARY OF THE INVENTION

The present invention provides new lipoxin analogs and methods for their preparation. The invention also provides methods of use of these compounds for the treatment of various forms of inflammation, autoimmune disorders, and diseases associated with undesired cell proliferation, such as cancer.

The present invention describes LX derivatives having aromatic rings fused on the tetraene moiety in a variety of configurations. These new compounds are structural analogs of natural LX compounds, such as lipoxin $A_4$, lipoxin $B_4$, 15-epi-lipoxin $A_4$, 15-epi-lipoxin $B_4$, and other related lipid mediators derived from polyunsaturated fatty acids other than arachidonic acid. The described compounds are readily prepared and have similar biological properties with the natural LX, while they have enhanced chemical and biological stability.

Provided herein are benzo-lipoxin analogues having the general structure 1

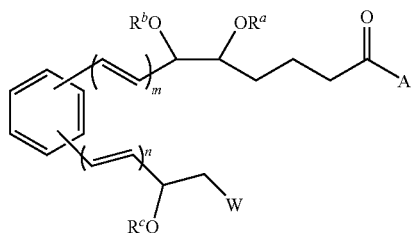

1 wherein:

A is hydroxy, alkoxy, aryloxy, amino, alkylamino, dialkylamino or —OM, where M is a cation selected from the group consisting of ammonium, tetra-alkyl ammonium, and the cations of sodium, potassium, magnesium and zinc;

W is hydrogen, alkyl, alkenyl, alkynyl, aryl, heteroaryl, halo, hydroxy, alkoxy, aryloxy, carboxy, amino, alkylamino, dialkylamino, acylamino, carboxamido, or sulfonamide;

$R^a$-$R^c$ are independently selected from a group costing of hydrogen, alkyl, aryl, acyl or alkoxyacyl;

the integer n is zero, one or two;

the integer m is one or two;

and wherein the two substituents on the benzene ring are either ortho-, meta- or para- Some preferred embodiments of the present invention are benzo-lipoxin analogues having one of the general structures 2-7,

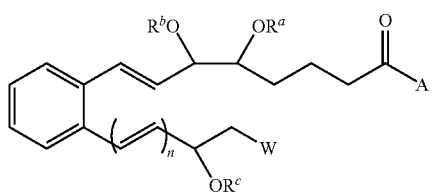

2

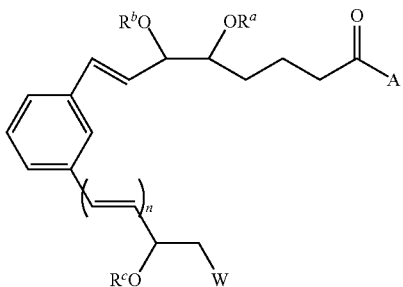

3

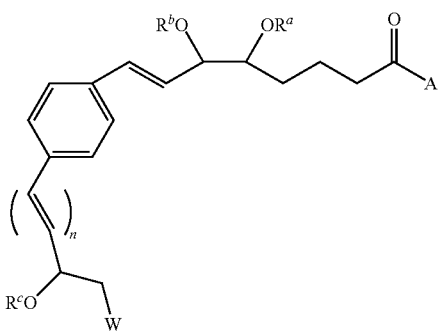

4

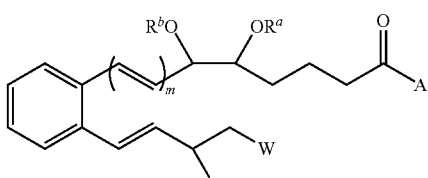

5

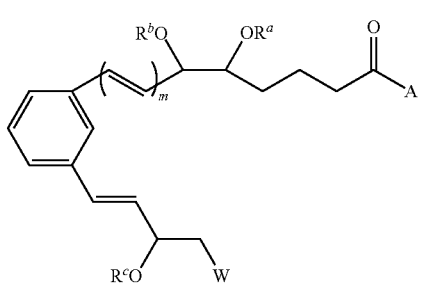

6

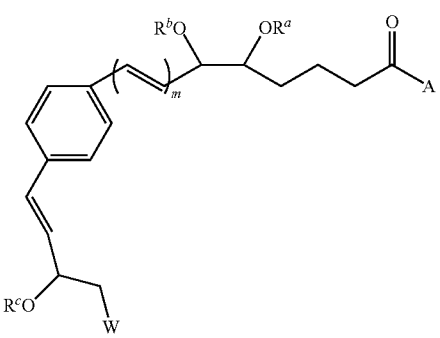

7 wherein:

A is hydroxy, alkoxy, aryloxy, amino, alkylamino, dialkylamino or —OM, where M is a cation selected from the group consisting of ammonium, tetra-alkyl ammonium, and the cations of sodium, potassium, magnesium and zinc;

W is hydrogen, alkyl, alkenyl, alkynyl, aryl, heteroaryl, halo, hydroxy, alkoxy, aryloxy, carboxy, amino, alkylamino, dialkylamino, acylamino, carboxamido, or sulfonamide;

$R^a$-$R^c$ are independently selected from a group costing of hydrogen, alkyl, aryl, acyl or alkoxyacyl;

the integer n is zero, one or two;

the integer m is one or two.

Additional preferred embodiments of the present invention are analogs of lipoxin A4 and have the stereochemistry designated in formulas 8-13.

8

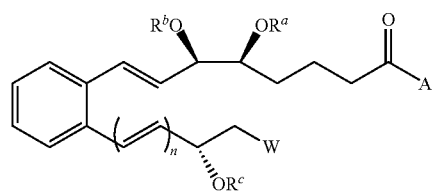

9

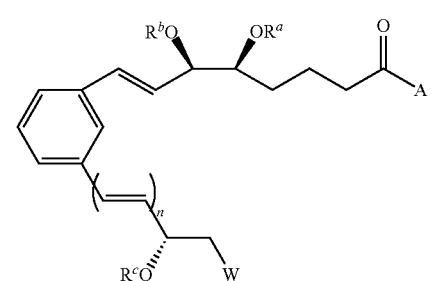

10

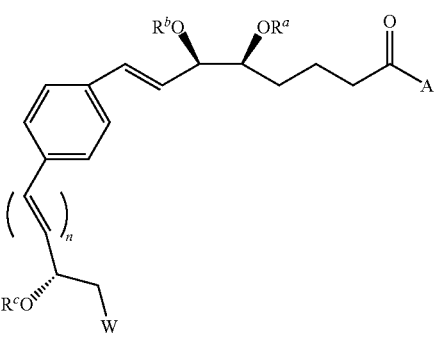

11

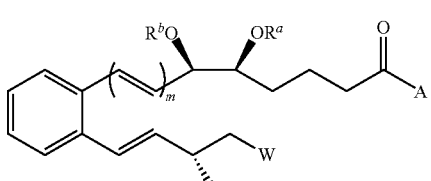

12

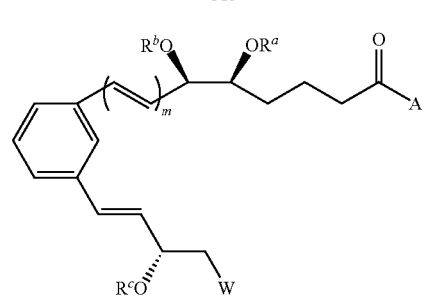

-continued

13

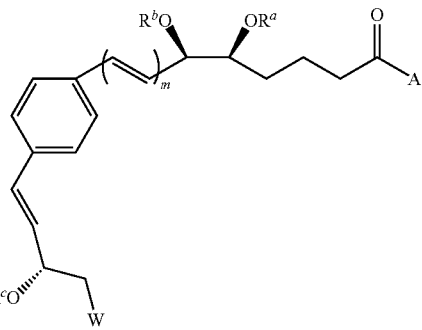

wherein:

A is hydroxy, alkoxy, aryloxy, amino, alkylamino, dialkylamino or —OM, where M is a cation selected from the group consisting of ammonium, tetra-alkyl ammonium, and the cations of sodium, potassium, magnesium and zinc;

W is hydrogen, alkyl, alkenyl, alkynyl, aryl, heteroaryl, halo, hydroxy, alkoxy, aryloxy, carboxy, amino, alkylamino, dialkylamino, acylamino, carboxamido, or sulfonamide;

$R^a$-$R^c$ are independently selected from a group costing of hydrogen, alkyl, aryl, acyl or alkoxyacyl;

the integer n is zero, one or two;

the integer m is one or two.

Additional preferred embodiments of the present invention are analogs of 15-epi-lipoxin A4 and have the stereochemistry designated in formulas 14-19.

14

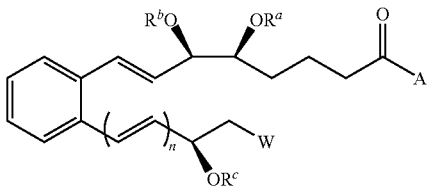

15

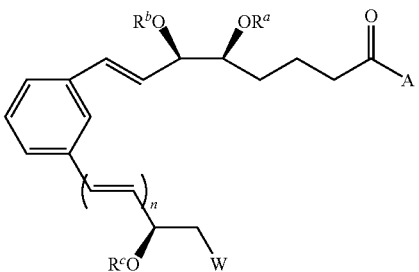

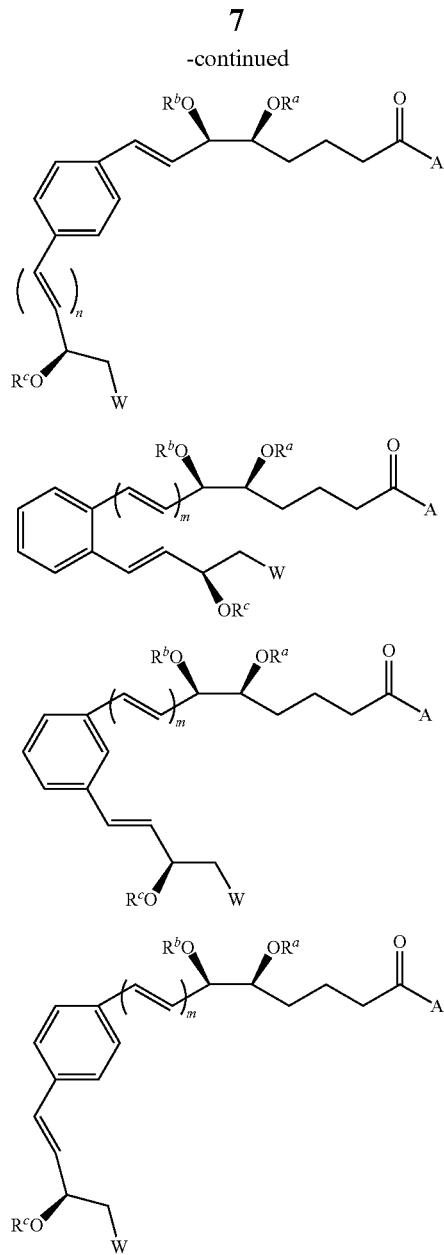

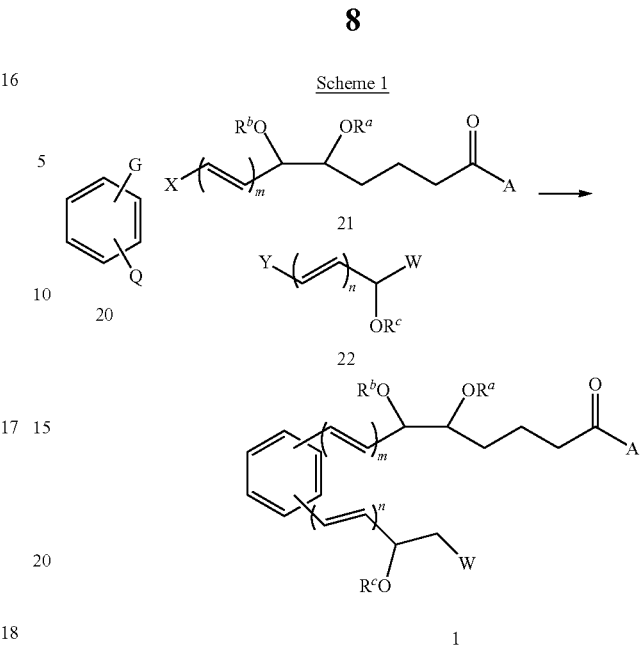

Scheme 1 wherein:
G, Q, X and Y are independently selected from a group consisting of bromo, chloro, iodo, triflyl, diazonium, iodonium, boronic acid, boronate, borinate, borate, trifluoroborate, stannyl, perfluorostannyl, silyl, zinc, magnesium or copper.

Compound 20 is first reacted with either 21 or 22 followed by reaction with the other, in the presence of a Pd, Ni or Cu catalyst, provided that in each case appropriate combinations of G, Q, X and Y are present in the reacting compounds.

Appropriate reaction combinations among 20+21 or 20+22 involve the combination of compound 20 having G or C selected from a group consisting of: bromo, chloro, iodo, triflyl, diazonium, iodonium and a compound 21 or 22 having X and Y independently selected from a group consisting of boronate, borinate, borate, trifluoroborate, stannyl, perfluorostannyl, silyl, zinc, magnesium or copper.

The coupling reactions among 20, 21 and 22 can also be carried out in sequence or in one pot. In particular embodiments, compounds 20, 21 and 22 can also be connected to a polymeric chain or other solid phase material.

The present invention also describes methods of use of the benzo lipoxin analogs for the treatment of various forms of inflammation, autoimmune disorders, and diseases associated with undesired cell proliferation, such as cancer.

wherein:
A is hydroxy, alkoxy, aryloxy, amino, alkylamino, dialkylamino or —OM, where M is a cation selected from the group consisting of ammonium, tetra-alkyl ammonium, and the cations of sodium, potassium, magnesium and zinc;

W is hydrogen, alkyl, alkenyl, alkynyl, aryl, heteroaryl, halo, hydroxy, alkoxy, aryloxy, carboxy, amino, alkylamino, dialkylamino, acylamino, carboxamido, or sulfonamide;

$R^a$-$R^c$ are independently selected from a group costing of hydrogen, alkyl, aryl, acyl or alkoxyacyl;

the integer n is zero, one or two;

the integer m is one or two.

Another aspect of the present invention is method for the synthesis of benzo lipoxin analogs. A common theme in the synthetic approach to these compounds is the use of iterative metal-mediated couplings of suitable intermediates (Scheme 1).

DETAILED DESCRIPTION OF THE INVENTION

A. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

As used herein, the nomenclature alkyl, alkoxy, carbonyl, etc. is used as is generally understood by those of skill in this art.

As used in this specification, alkyl groups can include straight-chained, branched and cyclic alkyl radicals containing up to about 20 carbons, or 1 to 16 carbons, and are straight or branched. Exemplary alkyl groups herein include, but are not limited to, methyl, ethyl, propyl, isopropyl, isobutyl, n-butyl, sec-butyl, tert-butyl, isopentyl, neopentyl, tert-pentyl and isohexyl. As used herein, lower alkyl refer to carbon chains having from about 1 or about 2 carbons up to about 6 carbons. Suitable alkyl groups may be saturated or unsaturated. Further, an alkyl may also be substituted one or more times on one or more carbons with substituents selected from a group consisting of C1-C15 alkyl, allyl, allenyl, alkenyl, C3-C7 heterocycle, aryl, halo, hydroxy, amino, cyano, oxo, thio, alkoxy, formyl, carboxy, carboxamido, phosphoryl, phosphonate, phosphonamido, sulfonyl, alkylsulfonate, arylsulfonate, and sulfonamide. Additionally, an alkyl group may contain up to 10 heteroatoms, in certain embodiments, 1, 2, 3, 4, 5, 6, 7, 8 or 9 heteroatom substituents. Suitable heteroatoms include nitrogen, oxygen, sulfur and phosphorous.

As used herein, "cycloalkyl" refers to a mono- or multicyclic ring system, in certain embodiments of 3 to 10 carbon atoms, in other embodiments of 3 to 6 carbon atoms. The ring systems of the cycloalkyl group may be composed of one ring or two or more rings which may be joined together in a fused, bridged or spiro-connected fashion.

As used herein, "aryl" refers to aromatic monocyclic or multicyclic groups containing from 3 to 16 carbon atoms. As used in this specification, aryl groups are aryl radicals which may contain up to 10 heteroatoms, in certain embodiments, 1, 2, 3 or 4 heteroatoms. An aryl group may also be optionally substituted one or more times, in certain embodiments, 1 to 3 or 4 times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

As used in this specification, a ring is defined as having up to 20 atoms that may include one or more nitrogen, oxygen, sulfur or phosphorous atoms, provided that the ring can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, phosphonate, phosphonamido, and sulfonyl, and further provided that the ring may also contain one or more fused rings, including carbocyclic, heterocyclic, aryl or heteroaryl rings.

As used herein, alkenyl and alkynyl carbon chains, if not specified, contain from 2 to 20 carbons, or 2 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, tetrazolyl, thienyl, pyridyl, pyrrolyl, N-methylpyrrolyl, quinolinyl and isoquinolinyl.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "halo", "halogen" or "halide" refers to F, Cl, Br or I.

As used herein, "haloalkyl" refers to an alkyl group in which one or more of the hydrogen atoms are replaced by halogen. Such groups include, but are not limited to, chloromethyl and trifluoromethyl.

As used herein, "alkoxy" refers to RO—, in which R is alkyl, including lower alkyl.

As used herein, "aryloxy" refers to RO—, in which R is aryl, including lower aryl, such as phenyl.

As used herein "subject" is an animal, typically a mammal, including human, such as a patient.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl ar heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl ar heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating a cancer.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

B. Compounds

Provided herein are benzo-lipoxin analogues having the general structure 1

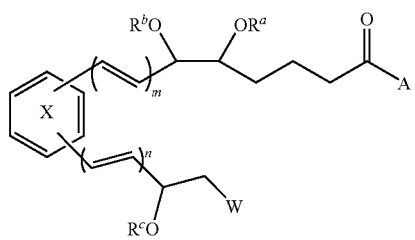

1 wherein:
- A is hydroxy, alkoxy, aryloxy, amino, alkylamino, dialkylamino or —OM, where M is a cation selected from the group consisting of ammonium, tetra-alkyl ammonium, and the cations of sodium, potassium, magnesium and zinc;
- W is hydrogen, alkyl, alkenyl, alkynyl, aryl, heteroaryl, halo, hydroxy, alkoxy, aryloxy, carboxy, amino, alkylamino, dialkylamino, acylamino, carboxamido, or sulfonamide;
- $R^a$-$R^c$ are independently selected from a group costing of hydrogen, alkyl, aryl, acyl or alkoxyacyl;
- the integer n is zero, one or two;
- the integer m is one or two;
- and wherein the two substituents on the ring X are either ortho-, meta- or para- In certain embodiments herein, W is alkyl or aryloxy. In other embodiments, W is butyl.

In other embodiments, W is aryloxy.

In certain embodiments herein, A is hydroxy or alkoxy.

Some preferred embodiments of the present invention are benzo-lipoxin analogues having one of the general structures 2-7,

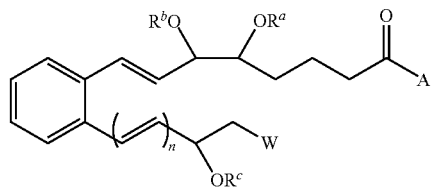

2

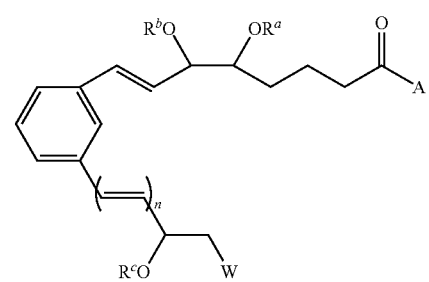

3

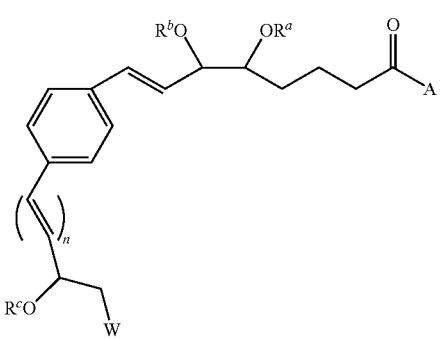

4

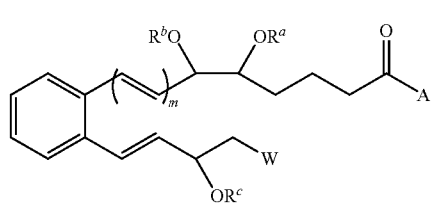

5

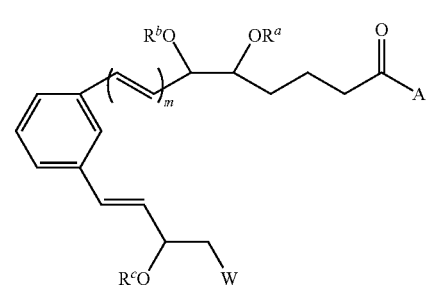

6

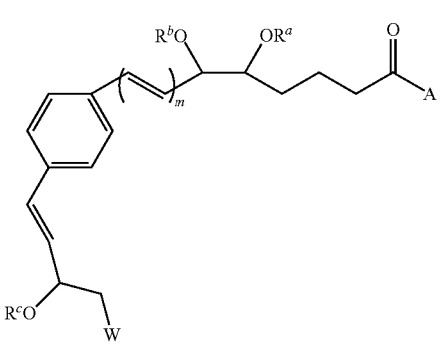

7 wherein:

A is hydroxy, alkoxy, aryloxy, amino, alkylamino, dialkylamino or —OM, where M is a cation selected from the group consisting of ammonium, tetra-alkyl ammonium, and the cations of sodium, potassium, magnesium and zinc;

W is hydrogen, alkyl, alkenyl, alkynyl, aryl, heteroaryl, halo, hydroxy, alkoxy, aryloxy, carboxy, amino, alkylamino, dialkylamino, acylamino, carboxamido, or sulfonamide;

$R^a$-$R^c$ are independently selected from a group costing of hydrogen, alkyl, aryl, acyl or alkoxyacyl;

the integer n is zero, one or two;

the integer m is one or two.

Additional preferred embodiments of the present invention are analogs of lipoxin A4 and have the stereochemistry designated in formulas 8-13.

8
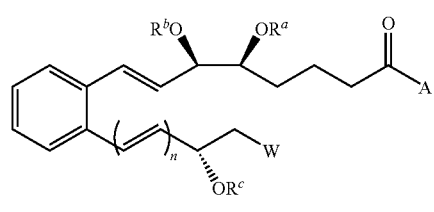

9
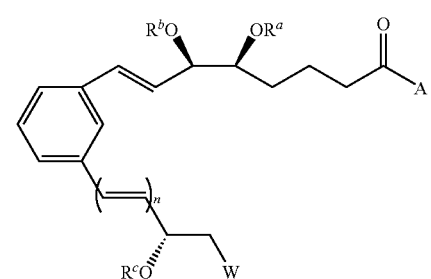

10
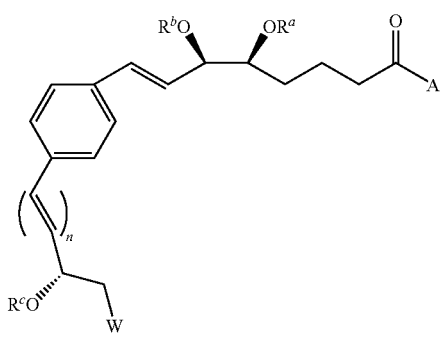

11
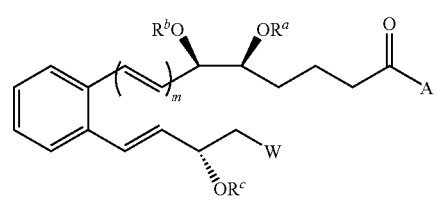

12
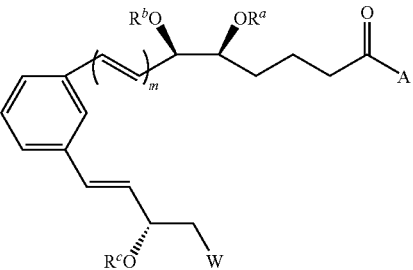

13
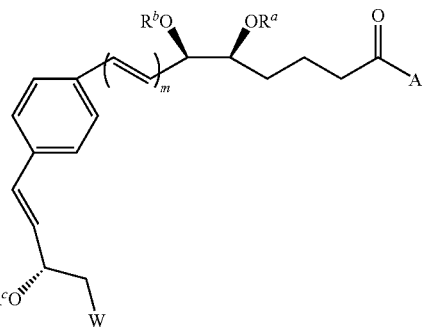

wherein:

A is hydroxy, alkoxy, aryloxy, amino, alkylamino, dialkylamino or —OM, where M is a cation selected from the group consisting of ammonium, tetra-alkyl ammonium, and the cations of sodium, potassium, magnesium and zinc;

W is hydrogen, alkyl, alkenyl, alkynyl, aryl, heteroaryl, halo, hydroxy, alkoxy, aryloxy, carboxy, amino, alkylamino, dialkylamino, acylamino, carboxamido, or sulfonamide;

$R^a$-$R^c$ are independently selected from a group costing of hydrogen, alkyl, aryl, acyl or alkoxyacyl;

the integer n is zero, one or two;

the integer m is one or two.

Additional preferred embodiments of the present invention are analogs of 15-epi-lipoxin A4 and have the stereochemistry designated in formulas 14-19.

14
15
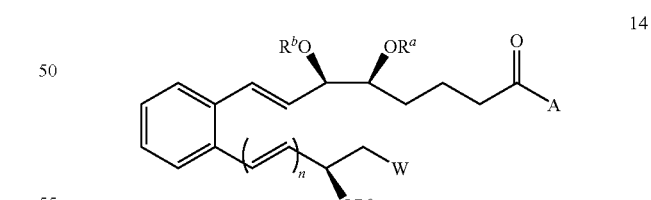

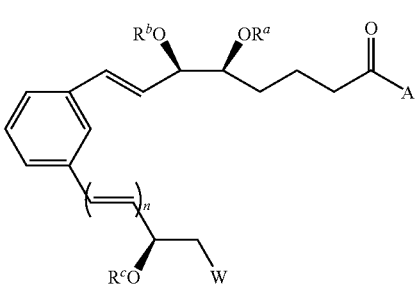

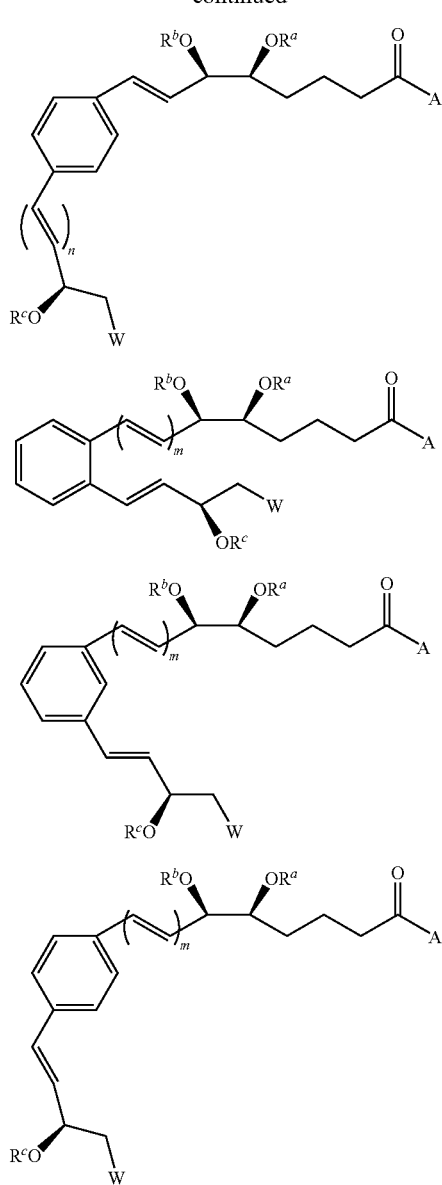

wherein:
A is hydroxy, alkoxy, aryloxy, amino, alkylamino, dialkylamino or —OM, where M is a cation selected from the group consisting of ammonium, tetra-alkyl ammonium, and the cations of sodium, potassium, magnesium and zinc;
W is hydrogen, alkyl, alkenyl, alkynyl, aryl, heteroaryl, halo, hydroxy, alkoxy, aryloxy, carboxy, amino, alkylamino, dialkylamino, acylamino, carboxamido, or sulfonamide;
$R^a$-$R^c$ are independently selected from a group costing of hydrogen, alkyl, aryl, acyl or alkoxyacyl;
the integer n is zero, one or two;
the integer m is one or two.

C. Preparation of the Compounds

The benzo lipoxin compounds provided herein are prepared as described herein. In certain embodiments, benzo lipoxin compounds of the general formula 1 can be prepared according to Scheme 1.

A common theme in the synthetic approach to these compounds is the use of iterative metal-mediated couplings of suitable intermediates (Scheme 1).

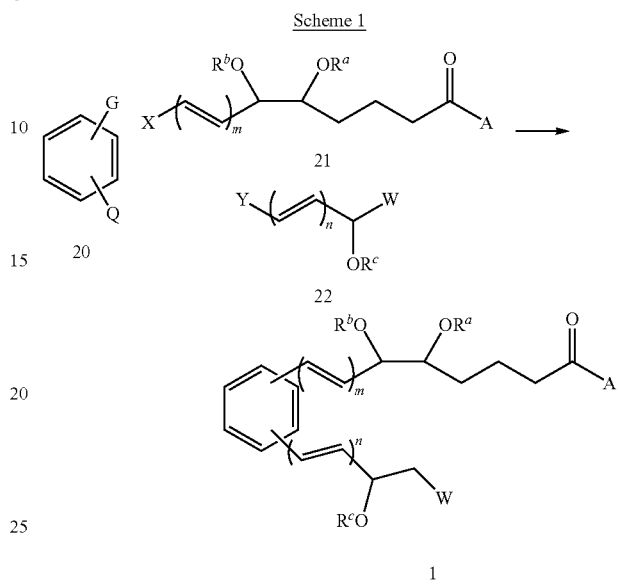

wherein:
G, Q, X and Y are independently selected from a group consisting of bromo, chloro, iodo, triflyl, diazonium, iodonium, boronic acid, boronate, borinate, borate, trifluoroborate, stannyl, perfluorostannyl, silyl, zinc, magnesium or copper.

Compound 20 is first reacted with either 21 or 22 followed by reaction with the other, in the presence of a Pd, Ni or Cu catalyst, provided that in each case appropriate combinations of G, Q, X and Y are present in the reacting compounds.

Appropriate reaction combinations among 20+21 or 20+22 involve the combination of compound 20 having G or C selected from a group consisting of: bromo, chloro, iodo, triflyl, diazonium, iodonium and a compound 21 or 22 having X and Y independently selected from a group consisting of boronate, borinate, borate, trifluoroborate, stannyl, perfluorostannyl, silyl, zinc, magnesium or copper.

The coupling reactions among 20, 21 and 22 can also be carried out in sequence or in one pot. In particular embodiments, compounds 20, 21 and 22 can also be connected to a polymeric chain or other solid phase material.

D. Formulation of Pharmaceutical Compositions

The pharmaceutical compositions provided herein contain therapeutically effective amounts of one or more of compounds provided herein in a pharmaceutically acceptable carrier.

The compositions contain one or more compounds provided herein. The compounds are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of conditions including, but not limited to, undesired cell proliferation, coronary restenosis, osteoporosis and syndromes characterized by chronic inflammation, autoimmune diseases and cardiovascular diseases.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated undesired cell proliferation, coronary restenosis, osteoporosis, syndromes characterized by chronic inflammation, autoimmune diseases and cardiovascular diseases as described herein.

Typically a therapeutically effective dosage should produce a serum concentration of active ingredient of from about 0.1 ng/ml to about 50-100 µg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing diseases or disorders associated with undesired cell proliferation, coronary restenosis, osteoporosis, syndromes characterized by chronic inflammation, autoimmune diseases and cardiovascular diseases as described herein. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, rectally, topically and locally. For oral administration, capsules and tablets are presently preferred. The compositions are in liquid, semi-liquid or solid form and are formulated in a manner suitable for each route of administration. Preferred modes of administration include parenteral and oral modes of administration. Oral administration is presently most preferred.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active ingredient, preferably 0.1-85%, typically 75-95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as diseases or disorders associated with undesired cell proliferation, coronary restenosis, osteoporosis, syndromes characterized by chronic inflammation, autoimmune diseases and cardiovascular diseases. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, preferably 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Articles of Manufacture

The compounds or pharmaceutically acceptable derivatives thereof can be packaged as articles of manufacture containing packaging material, a compound or pharmaceutically acceptable derivative thereof provided herein, which is used for treatment, prevention or amelioration of one or more symptoms associated with undesired cell proliferation, coronary restenosis, osteoporosis, syndromes characterized by chronic inflammation, autoimmune diseases and cardiovascular diseases condition, and a label that indicates that the compound or pharmaceutically acceptable derivative thereof is used for treatment, prevention or amelioration of one or more symptoms associated with undesired cell proliferation, coronary restenosis, osteoporosis, syndromes characterized by chronic inflammation, autoimmune diseases and cardiovascular diseases.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disorder associated with undesired cell proliferation, coronary restenosis, osteoporosis, syndromes characterized by chronic inflammation, autoimmune diseases and cardiovascular diseases condition.

E. Methods of use of the Compounds and Compositions

The compounds of the invention are structural analogs of naturally-occurring molecules that are known to have biological activity against a wide variety of targets, including diseases or conditions associated with inflammation or inflammatory response, undesired cell proliferation, such as cancer, and cardiovascular diseases. As such, the compounds of the invention are expected to have similar activity against those targets.

Accordingly, in one aspect the invention features methods of ameliorating or treating diseases or conditions associated with inflammation or inflammatory response, involving the administration to a subject of a therapeutically effective amount of a compound or compounds of the invention, such that inflammation or an inflammatory response are significantly reduced or eliminated in the subject. A significant reduction includes the reduction or elimination of a symptom or symptoms associated with the inflammation or inflammatory response.

In another aspect, the invention features methods of ameliorating or treating diseases or conditions associated with undesired cell proliferation, such as cancer, involving the administration to a subject of an effective amount of a compound or compounds of the invention. In general, an effective amount is an amount sufficient to ensure adequate exposure of a target cell population, such that abnormal cell proliferation is substantially slowed or halted. A target population is a population of cells undergoing abnormal cell proliferation, such as cancerous and/or tumorous growth.

The invention will be further described in the following examples, which are illustrative only, and which are not intended to limit the scope of the invention described in the claims.

EXAMPLES

In the following examples, efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric. Starting materials used in these examples are generally either commercially available or can be readily prepared from commercially available reagents by a procedure involving one or more steps.

The following Schemes show examples of the synthesis of several benzo lipoxin analogs. A common building block, compound 23 is prepared according to Scheme 2, while Schemes 3-6 outline the synthesis of selected example of benzo-lipoxin analogues.

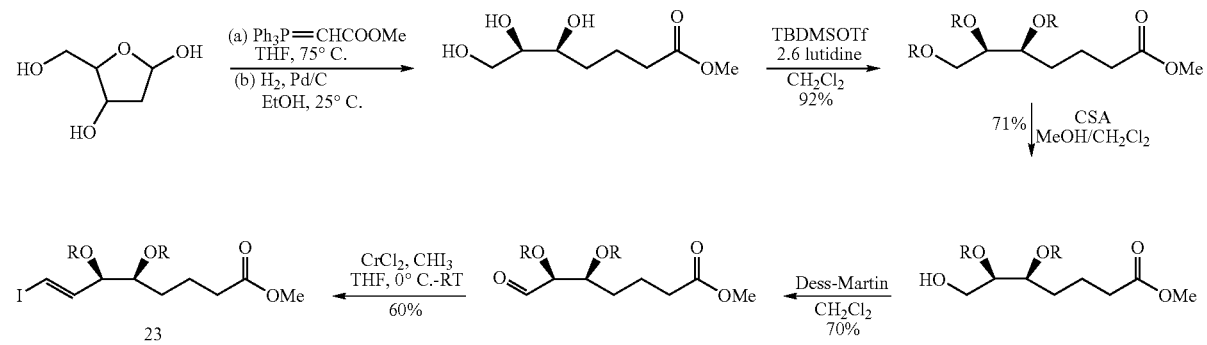

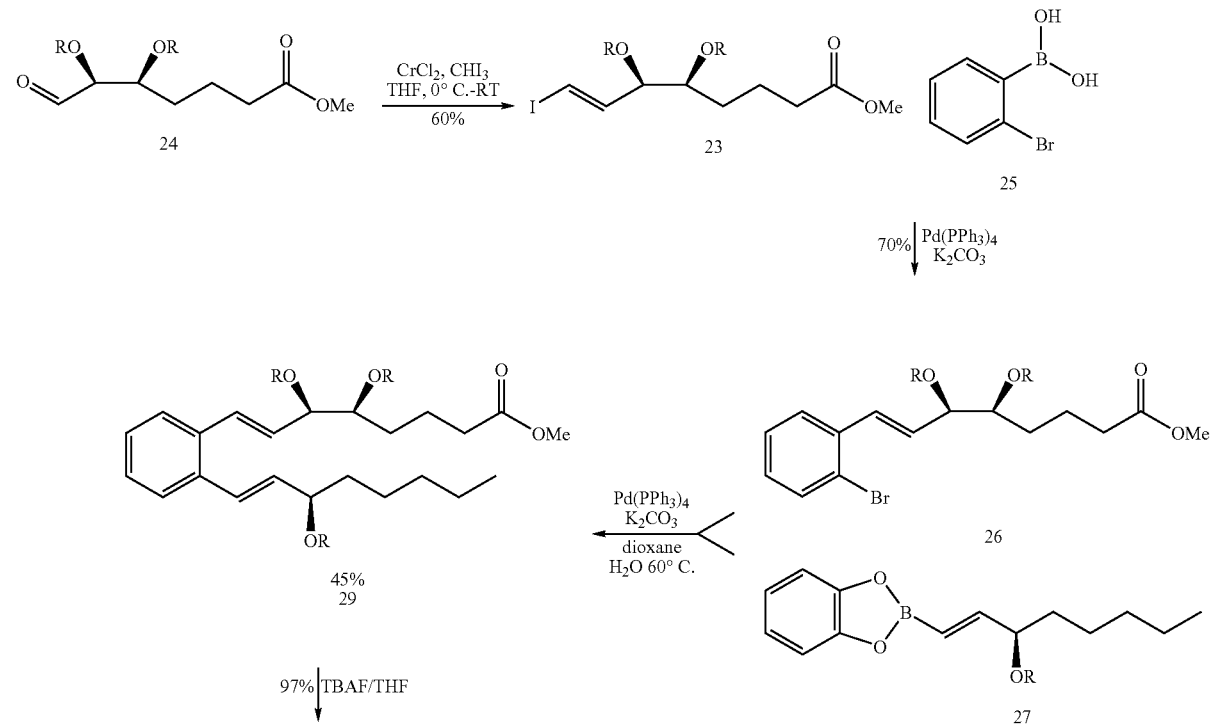

29 30
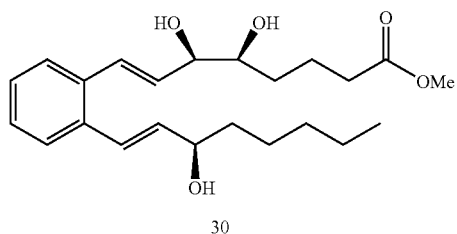
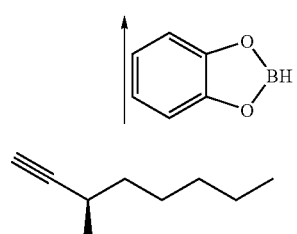
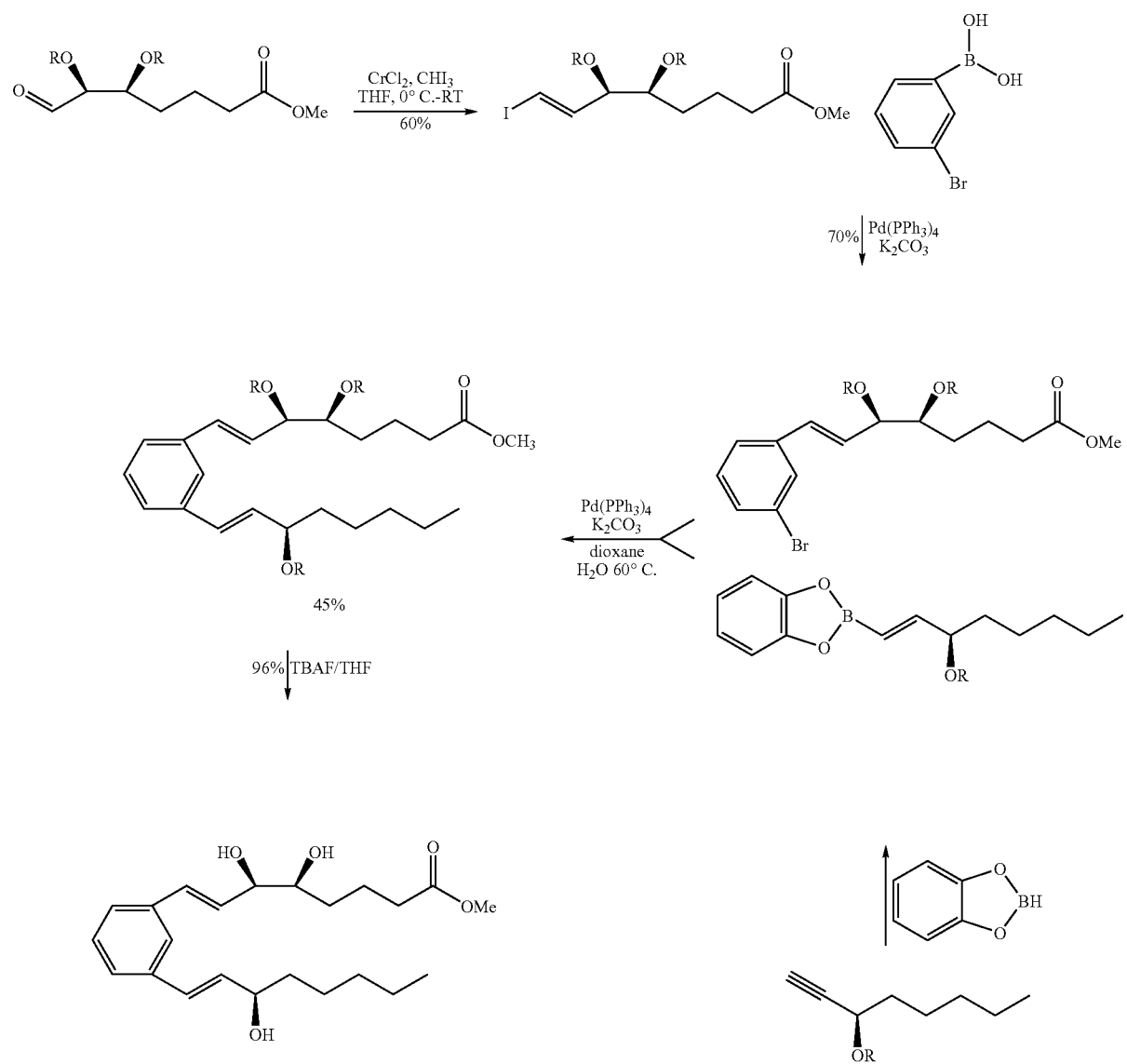

Scheme 5
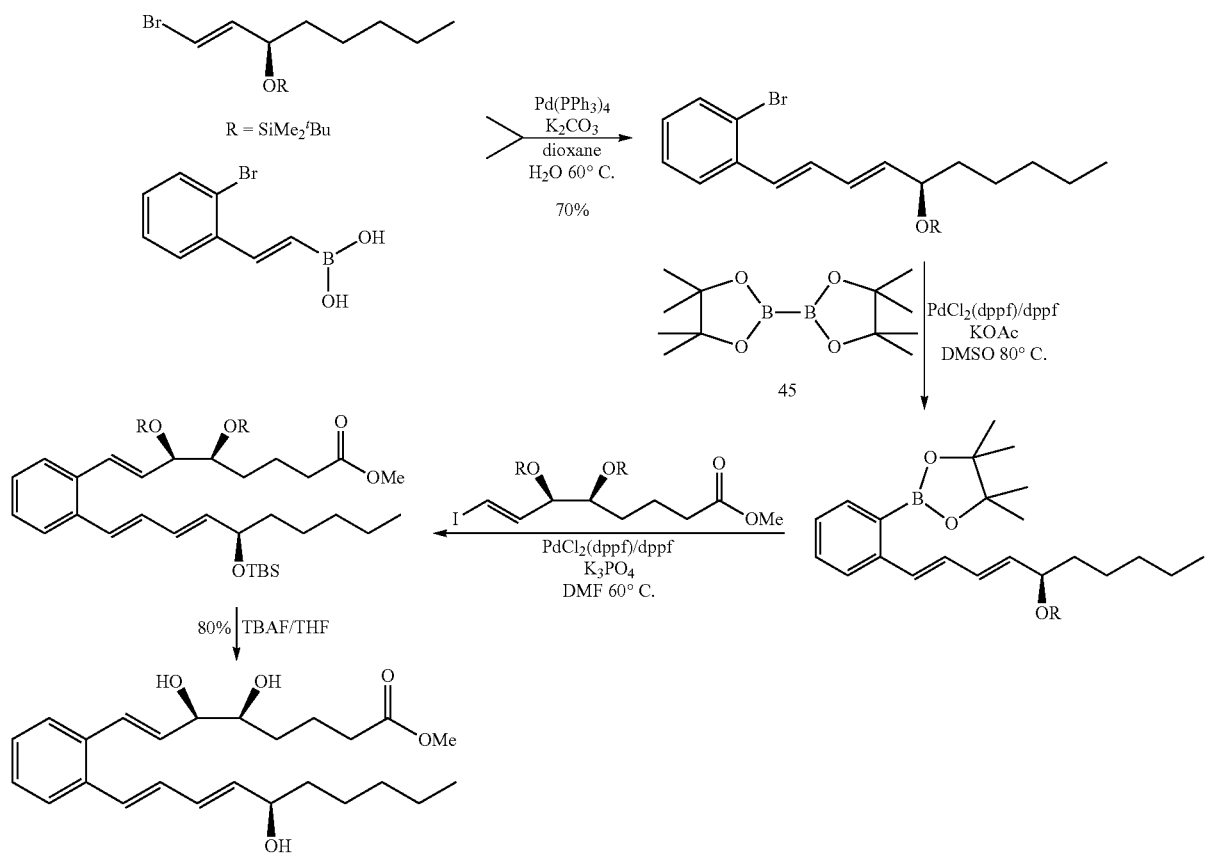
Scheme 6
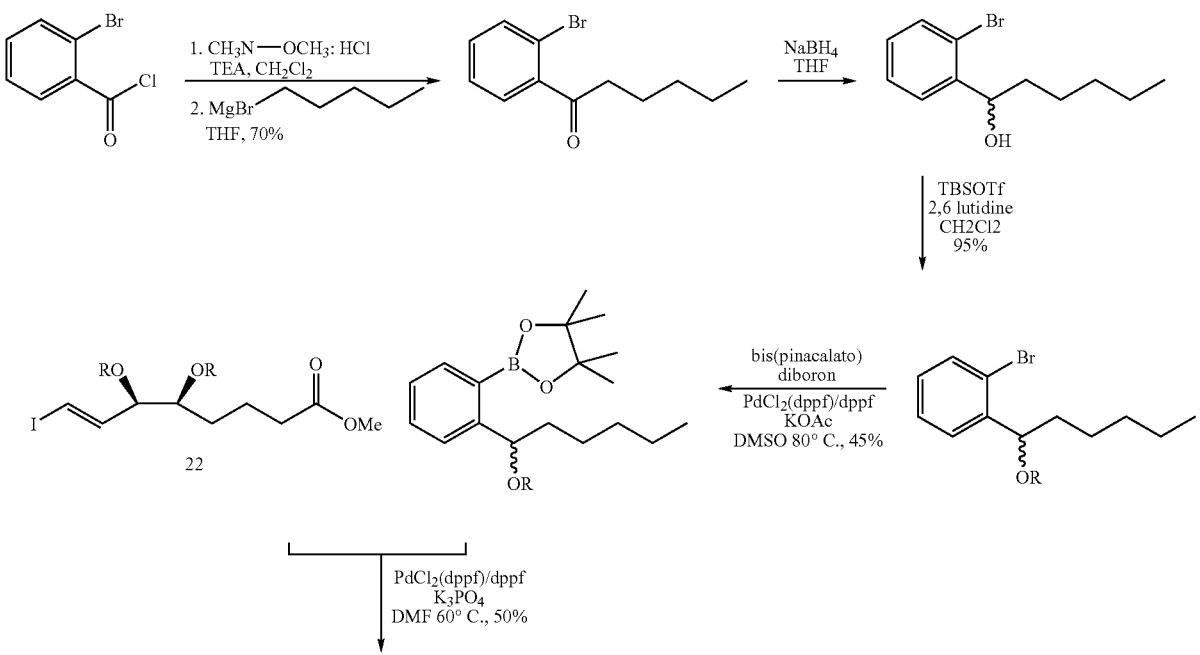

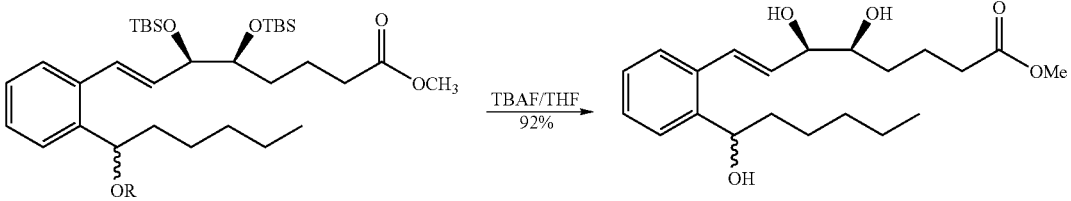

Example 1

(5S,6R,E)-methyl 5,6-dihydroxy-8-(2((R,E)-3-hydroxyoct-1-enyl)phenyl)oct-7-enoate

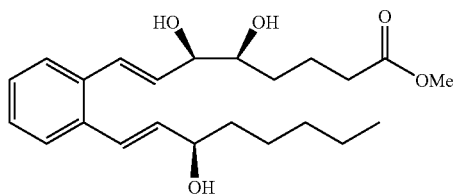

Step 1: A solution of (5S,6S)-methyl 5,6-bis(tert-butyldimethylsilyloxy)-7-oxoheptanoate (389 mg, 0.929 mmol) and iodoform (2.19 g, 5.57 mmol) in THF (20 mL) was allowed it to stir for about 10 min. In a separate round bottom flask added chromium chloride (II) (1.36 mg, 11.1 mmol) and dissolved it in THF (10 mL) and cooled the reaction mixture to 0° C. The aldehyde and iodoform mixture were transferred to a stirring solution of chromium chloride at 0° C., warmed to room temperature and allowed to stir for 3 h. The reaction was quenched with water, extracted with ether, dried, and concentrated. Purification by flash chromatography (silica gel, hexanes) afforded 200 mg (40% yield) of (5S,6R,E)-methyl 5,6-bis(tert-butyldimethylsilyloxy)-8-iodooct-7-enoate. $^1$H NMR (250 MHz, CDCl$_3$): δ 6.46 (dd, J=14.9 Hz, J=7.2 Hz 1H), 6.18 (d, J=15.4 Hz, 1H), 3.85 (m, 1H), 3.63 (s, 3H), 3.52 (m, 1H), 2.27 (t, J=7.1 Hz, 3H), 1.62 (m, 2H), 1.47 (m, 2H), 0.850 (s, 9H), 0.849 (s, 9H), 0.023 (s, 6H), 0.013 (s, 3H), −0.005 (s, 3H).

Step 2: The product from Step 1 (64 mg, 0.127 mmol), was placed in a microwave tube together with commercially available 2-bromo phenyl boronic acid (27 mg, 0.129 mmol), potassium carbonate (51 mg, 0.372 mmol), Pd(PPh$_3$)$_4$ (7 mg, 5 mol %), and dioxane (1.5 mL). The tube was sealed, degassed, purged with argon, and heated to 60° C. The reaction mixture was stirred for 12 h, after which time it was quenched with saturated ammonium chloride, extracted with ether, dried, and concentrated. The product was purified by preparatory TLC (silica plate, 8% ethyl acetate/hexanes) to afford 50 mg (70%) of (5S,6R,E)-methyl 8-(2-bromophenyl)-5,6-bis(tert-butyldimethylsilyloxy)oct-7-enoate. $^1$H NMR (360 MHz, CDCl$_3$): δ 7.49 (dd, J=20 Hz, 7.7 Hz, 2H), 7.24 (t, J=8.3 Hz, 1H), 7.06 (t, J=7.4 Hz, 1H), 6.84 (d, J=15.4 Hz, 1H), 6.10 (dd, J=15.9 Hz, 7.3 Hz), 4.48 (m, 1H), 3.63 (s, 3H), 2.29 (t, J=7.5 Hz), 1.71 (m, 2H), 1.53 (m, 2H), 0.894 (s, 9H), 0.857 (s, 9H), 0.084 (s, 3H), 0.080 (s, 6H), 0.016 (s, 3H). $^{13}$C NMR (500 MHz, CDCl$_3$): δ 136.90, 136.61, 132.903, 129.93, 128.59, 127.42, 126.99, 77.0, 76.0, 50.9, 34.35, 33.04, 29.70, 25.99, 20.67, 10.17, −3.95, −4.76.

Step 3: Commercially available R-octyn-ol (146 mg, 0.611 mmol) was dissolved in DCM (4 mL), and cooled to 0° C., followed by addition of 2,6 lutidine (1.54 mg, 4.36 mmol) and tetra-butyldimethylsilyl-triflate (785 mg, 2.97 mmol). The reaction mixture was allowed to stir overnight, quenched with water, and extracted with ether. Flash chromatography (silica gel, hexanes) afforded 463 mg (90%) of the protected alcohol. To the protected alcohol (146 mg, 0.611 mmol) was added catechol borane (73 mg, 0.611 mmol) neat, heated to 60° C. and allowed to stir overnight generating (5S,6R,E)-methyl 8-(2-bromophenyl)-5,6-bis(tert-butyldimethylsilyloxy)oct-7-enoate. $^1$H NMR (250 MHz, CDCl$_3$): δ 7.37 (m, 1H), 7.21 (m, 2H), 7.11 (J, J=4.6 Hz, 2H), 6.99 (m, 1H), 6.13 (dd, J=18 Hz, 1.8 Hz, 1H), 4.43 (s, 1H), 1.75-1.63 (m, 2H), 1.58-1.35 (m, 6H), 1.08 (s, 3H), 1.03 (s, 9H), 0.239 (s, 3H), 0.220 (s, 3H).

Step 4: In a microwave tube added the product of Step 2 (35 mg, 0.070 mmol), the product of Step 3 (23 mg, 0.064 mmol), potassium carbonate (25 mg, 0.183 mmol), Pd(PPh3)4 (3.5 mg, 5 mol %), and dioxane/water (1/3:2/3, 3 mL). The tube was sealed, degassed, purged with argon, heated to 80° C. and allowed to stir from 24 h. The reaction was quenched with saturated ammounium chloride, extracted with ether, dried and concentrated. Purification with preparatory TLC (silica plate, 5% ethyl acetate/hexane) afforded 18.2 mg (40%) of (5S,6R,E)-methyl 5,6-bis(tert-butyldimethylsilyloxy)-8-(2((R,E)-3-(tert-butyldimethylsilyloxy)oct-1-enyl)phenyl)oct-7-enoate. $^1$H NMR (360 MHz, CDCl$_3$): δ 7.37 (m, 2H), 7.19 (m, 2H), 6.72 (dd, J=15.3 Hz, 3.4 Hz, 2H), 6.06-5.96 (m, 2H), 4.21 (m, 1H), 4.09 (m, 1H), 3.65 (m, 1H), 3.61 (s, 3H), 2.27 (t, J=7.2 Hz, 2H), 1.75-1.60 (m, 4H), 1.54-1.44 (m, 8H), 1.29-1.21 (m, 5H), 0.890 (s, 9H), 0.879 (s, 9H), 0.057 (s, 6H), 0.031 (s, 3H), 0.019 (s, 3H), 0.008 (s, 3H), −0.004 (s, 3H). $^{13}$C (360 MHz, CDCl$_3$): δ 173.94, 136.20, 135.54, 135.06, 132.63, 128.66, 127.46, 127.34, 126.54, 126.48, 126.24, 77.45, 76.07, 73.87, 51.45, 38.46, 34.35, 32.88, 31.85, 26.01, 25.00, 22.68, 14.09, −3.99, −4.78.

Step 5: The product of Step 4 was dissolved in THF (1 mL) and cooled to 0° C. Tetra-butyl ammonium fluoride (10 μL, 0.078 mmol) was added and the reaction mixture was warmed to RT and allowed to stir overnight. The reaction mixture was quenched with saturated ammonium chloride, extracted with ether, dried and concentrated. Purification by preparatory TLC (silica plate, 5% MeOH/Ethyl acetate) afforded 6.1 mg (96.8%) of (5S,6R,E)-methyl 5,6-dihydroxy-8-(2((R,E)-3-hydroxyoct-1-enyl)phenyl)oct-7-enoate. $^1$H NMR (250 Hz, CDCl$_3$): δ 7.38 (m, 2H), 7.22 (m, 2H), 6.86 (t, J=15.4 Hz, 1H), 6.07 (m, 1H), 4.27 (m, 1H), 3.77 (m, 1H), 3.63 (m, 1H), 3.46 (q, J=14 Hz, 6.9 Hz, 1H), 2.35 (t, J=7.5 Hz, 2H), 1.81-1.53 (m, 4H), 1.32-1.16 (m, 7H), 0.915-0.789 (m, 4H). $^{13}$C (500 NMR C$_6$D$_6$): δ 173.79, 136.18, 136.12, 135.98, 131.59, 130.34, 136.18, 131.59, 130.34, 128.53, 128.20, 127.81, 127.68, 127.62, 127.47, 127.13, 76.02, 74.36, 72.65, 51.01, 37.92, 33.83, 32.22, 30.15, 25.58, 23.05, 21.57, 14.24.

Example 2

(5S,6R,E)-methyl 5,6-dihydroxy-8-(3((R,E)-3-hydroxyoct-1-enyl)phenyl)oct-7-enoate

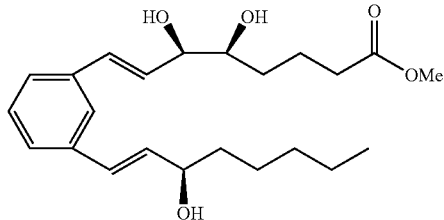

Prepared similar to Example 1. $^1$H NMR (250 MHz, CDCl$_3$): δ 7.46 (s, 1H), 7.23 (m, 3H), 6.59 (dd, J=20 Hz, 15.7 Hz, 2H), 6.25 (m, 2H), 4.21 (m, 1H), 3.75 (m, 1H), 3.64 (s, 3H), 3.45 (m, 1H), 2.35 (t, J=7.5 Hz, 2H), 1.39-1.20 (m, 11H), 0.870 (m, 4H). $^{13}$C NMR (250 MHz, CDCl$_3$): δ 176.10. 136.62, 136.62, 133.10, 133.03, 129.85, 128.86, 127.24, 126.08, 125.86, 124.63, 75.88, 73.81, 73.08, 51.61, 37.36, 33.73, 31.79, 31.49, 29.71, 25.13, 22.62, 21.09, 14.01.

Example 3

(5S,6R,E)-methyl 5,6-dihydroxy-8-(2((R,1E,3E)-5-hydroxydeca-1,3-dienyl)phenyl)oct-7-enoate

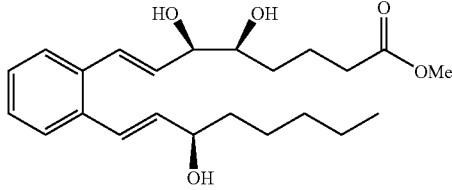

Prepared similar to Example 1. $^1$H NMR (250 MHz, CDCl$_3$): δ 7.46-7.35 (m, 2H), 7.29-7.17 (m, 2H), 7.10 (m, 1H), 6.87 (dd, J=29.9 Hz, 15.4 Hz, 1H), 6.63 (m, 1H), 6.39 (m, 1H), 6.11 (dd, J=16.2 Hz, 7.2 Hz), 5.80 (dd, J=14.7 Hz, 6.7 Hz), 4.27 (m, 1H), 3.74 (m, 1H), 3.45 (m, 1H), 3.63 (s, 3H), 2.32 (t, J=2.1 Hz, 2H), 1.34-1.20 (m, 8H), 0.902-0.820 (m, 6H). $^{13}$C NMR (500 MHz, CDCl$_3$): δ 172.11, 137.25, 135.48, 134.91, 130.73, 130.59, 129.84, 129.79, 128.26, 127.92, 127.62, 126.86, 126.08, 75.91, 73.87, 72.65, 51.62, 37.33, 33.79, 31.53, 29.69, 25.11, 2 2.59, 21.12, 13.98.

Example 4

(5S,6R,E)-methyl 5,6-dihydroxy-8-(2-(1-hydroxyhexyl)phenyl)oct-7-enoate

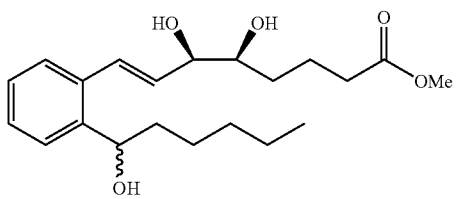

Step 1. Triethylamine (126 mg, 2.50 mmol) and O,N, dimethyl hydroxylamine (304 mg, 2.50 mmol) were dissolved in DCM and cooled to −10° C., after which time commercially available 2-bromobenzoyl chloride (500 mg, 2.27 mmol) was added, followed by addition of more TEA (126 mg, 2.50 mmol). The reaction was warmed to RT and allowed to stir overnight. DCM was removed, diluted with ether, acidified with 1N HCl, neutralized with saturated bicarbonate, extracted with ether, dried and collected. The resulting amide was dissolved in THF, cooled to −78° C., followed by addition of pentyl magnesium bromide (925 μL, 1.85 mmol), and allowed to stir for 90 min. The reaction was quenched with ammonium chloride, extracted with ether, dried and concentrated. Purification with flash chromatography (silica gel, 10% ethyl acetate/hexanes) afforded the desired ketone in 70% yield (400 mg). $^1$H NMR (250 MHz, CDCl$_3$): δ 8.0 (m, 1H), 7.70 (dd, J=8 Hz, 2 Hz, 2H), 7.57-7.21 (m, 2H), 2.94 (t, J=7 Hz, 2H), 1.72 (m, 2H), 1.34 (m, 2H), 1.21 (m, 2H), 0.892 (m, 3H).

Step 2. The product of Step 1 (109 mg, 0.428 mmol) was dissolved in MeOH (5 mL) followed by addition of sodium borohydride (32 mg, 0.856 mmol). The reaction mixture was allowed to stir for 1 hour, after which time it was quenched with 1 N HCl, extracted with ether, dried, and concentrated. Preparatory TLC (silica plate, 20% ethyl acetate/hexane) afforded the free alcohol in (109 mg) 90% yield. The alcohol (109 mg, 0.428 mmol) was dissolved in DCM (5 mL) and 2,6 lutidine (169 mg, 0.642 mmol), and tetra-butyldimethyl silyl triflate (100 mg, 0.940 mmol) were added and the reaction mixture was stirred overnight. The reaction was quenched with saturated ammonium chloride, extracted with ether, dried and concentrated. Preparatory TLC (silica plate, hexanes) afforded the protected alcohol in (150 mg) 95% yield. $^1$H NMR (360 MHz, CDCl$_3$): δ 7.57 (dd, J=7.8 Hz, 2.2 Hz, 1H), 7.43 (dd, J=8.1 Hz, J=1.5 Hz, 1H), 7.19 (m, 1H), 7.04 (m, 1H), 4.99 (m, 1H), 4.56 (m, 1H), 1.56 (m, 2H), 1.24 (m, 6H), 0.868 (s, 9H), 0.846 (s, 3 H), 0.023 (s, 3H).

Step 3. In a microwave tube added the product of Step 2 (16 mg, 0.037 mmol), bispinacaloto diboron (10 mg, 0.42 mmol), potassium acetate (11 mg, 0.11 mmol), PdCl$_2$(dppf) (1 mg, 3 mol %), dppf (1.25 mg, 6 mol %), and DMSO (226 μL) were added. The tube was sealed, degassed, purged with argon, and heated to 80° C. The reaction mixture was allowed to stir for 16 h, after which time the reaction was quenched with ammonium chloride, extracted with ether, dried and concentrated. Purification by preparatory TLC (silica plate, 5% ethyl acetate/hexanes) afforded the boronic pinacol ester.

Step 4. In a microwave tube added the product of Step 1 (Example 1) (5.7 mg, 0.011 mmol), the product of Step 3 (5 mg, 0.11 mmol) (3.xx), potassium phosphate (6.7 mg, 0.032 mmol), PdCl$_2$(dppf) (1 mg, 3 mol %), dppf (1.2 mg, 6 mol %), and DMF (150 μL). The tube was sealed, degassed, purged with argon, and heated to 60° C. The reaction mixture was allowed to stir for 16 h, after which time it was quenched with saturated ammonium chloride, extracted with ether, dried and concentrated. Purification by preparatory TLC afforded 3.6 mg (45% yield) of (5S,6R,E)-methyl 5,6-bis(tert-butyldimethylsilyloxy)-8-(2-(1-(tert-butyldimethylsilyloxy)hexyl)phenyl)oct-7-enoate. $^1$H NMR (250 MHz, CDCl$_3$): δ 7.45 (m, 1H), 7.35 (m, 1H), 7.16 (m, 2H), 6.75 (m, 1H), 6.01 (m, 1H), 4.91 (m, 1H), 4.12 (m, 1H), 3.64 (s, 3H), 2.22 (t, J=7.1 Hz, 2H), 1.64-1.45 (m, 4H), 1.31-1.12 (m, 11H), 0.911 (s, 9H), 0.810 (s, 18 H), 0.101 (s, 3H), 0.005 (s, 3H), −0.01 (s, 3H), −0.02 (s, 3H), −0.199, (s, 3H), −0.201 (s, 3H).

Step 4. Performed similarly to Step 5 (Example 1) to give (5S,6R,E)-methyl 5,6-dihydroxy-8-(2-(1-hydroxyhexyl)phenyl)oct-7-enoate. $^1$H NMR (500 MHz, CDCl$_3$): δ 7.46 (m, 2H), 7.31 (m, 2H), 7.04 (d, J=15 Hz, 1H), 6.13 (m, J=16.3 Hz, 7.1 Hz, 1H), 4.99 (m, 1H), 4.30 (m, 1H), 3.79 (m, 1H), 3.67 (m, 1H), 2.38 (m, 2H), 1.87 (m, 2H), 1.74 (m, 4H), 1.31 (m, 4H), 1.22 (m, 3H). $^{13}$C NMR (500 MHz, CDCl$_3$): δ 172.11, 130.14, 128.27, 128.12, 127.51, 126.54, 125.75, 77.20, 73.49, 71.09, 38.38, 31.71, 29.78, 25.67, 22.58, 21.87, 18.80, 13.99.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations and/or methods of use provided herein, may be made without departing from the spirit and scope thereof. U.S. patents and publications referenced herein are incorporated by reference.

The provided benzo lipoxin analogs exhibit anti-inflammatory properties in various inflammation models.

A number of embodiments of the invention have been described. Nevertheless, it will be understood that various modifications may be made without departing from the spirit and scope of the invention. Accordingly, other embodiments are within the scope of the following claims.

What is claimed is:

1. A compound selected from a group consisting of:

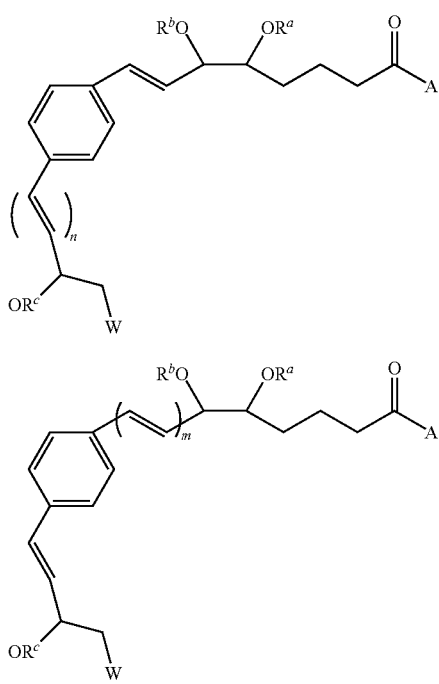

wherein:
A is hydroxy, alkoxy, aryloxy, amino, alkylamino, dialkylamino or —OM, where M is a cation selected from the group consisting of ammonium, tetra-alkyl ammonium, and the cations of sodium, potassium, magnesium and zinc;
W is hydrogen, alkyl, alkenyl, alkynyl, aryl, heteroaryl, halo, hydroxy, alkoxy, aryloxy, carboxy, amino, alkylamino, dialkylamino, acylamino, carboxamido, or sulfonamide;
$R^a$-$R^c$ are independently selected from a group costing of hydrogen, alkyl, aryl, acyl or alkoxyacyl;
the integer n is zero, one or two;
the integer m is one or two.

2. The compound of claim 1, wherein W is alkyl or aryloxy.
3. The compound of claim 1, wherein W is butyl.
4. The compound of claim 1, wherein W is aryloxy.
5. The compound of claim 1, wherein A is hydroxy or alkoxy.
6. The compound of claim 1, wherein the compound is selected from a group consisting of:

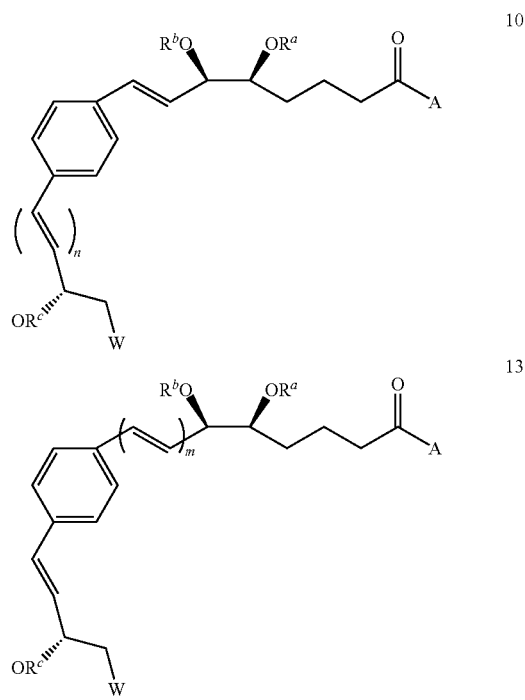

wherein:
A is hydroxy, alkoxy, aryloxy, amino, alkylamino, dialkylamino or —OM, where M is a cation selected from the group consisting of ammonium, tetra-alkyl ammonium, and the cations of sodium, potassium, magnesium and zinc;
W is hydrogen, alkyl, alkenyl, alkynyl, aryl, heteroaryl, halo, hydroxy, alkoxy, aryloxy, carboxy, amino, alkylamino, dialkylamino, acylamino, carboxamido, or sulfonamide;
$R^a$-$R^c$ are independently selected from a group costing of hydrogen, alkyl, aryl, acyl or alkoxyacyl;
the integer n is zero, one or two;
the integer m is one or two.

7. The compound of claim 1, wherein the compound is selected from a group consisting of:

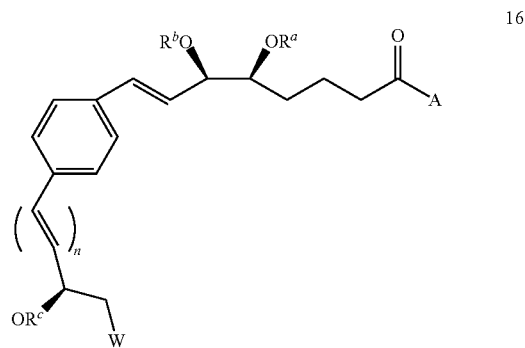

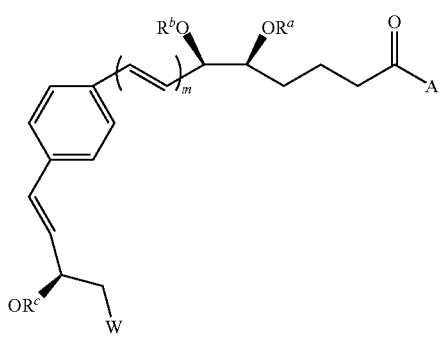

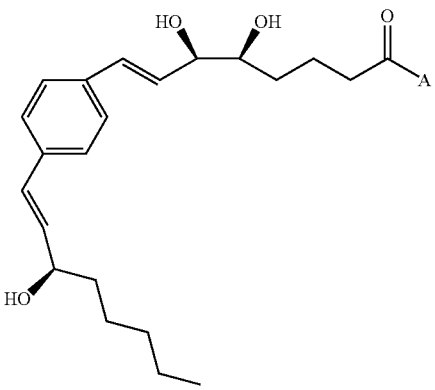

wherein:
  A is hydroxy, alkoxy, aryloxy, amino, alkylamino, dialkylamino or —OM, where M is a cation selected from the group consisting of ammonium, tetra-alkyl ammonium, and the cations of sodium, potassium, magnesium and zinc;
  W is hydrogen, alkyl, alkenyl, alkynyl, aryl, heteroaryl, halo, hydroxy, alkoxy, aryloxy, carboxy, amino, alkylamino, dialkylamino, acylamino, carboxamido, or sulfonamide;
  $R^a$-$R^c$ are independently selected from a group costing of hydrogen, alkyl, aryl, acyl or alkoxyacyl;
  the integer n is zero, one or two;
  the integer m is one or two.

8. A compound selected from a group consisting of:

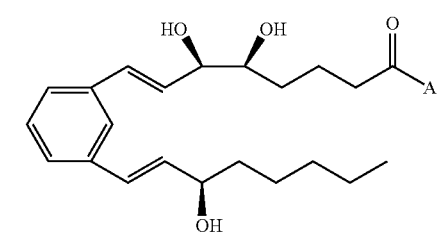

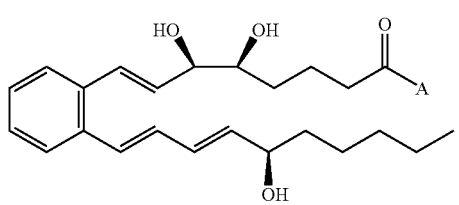

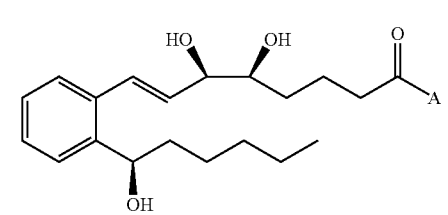

wherein:
  A is hydroxy, alkoxy, aryloxy, amino, alkylamino, dialkylamino or —OM, where M is a cation selected from the group consisting of ammonium, tetra-alkyl ammonium, and the cations of sodium, potassium, magnesium and zinc.

9. A pharmaceutical composition, comprising: a compound according to claim 1; and a pharmaceutically acceptable carrier.

10. An article of manufacture, comprising packaging material, the compound of claim 1, or a pharmaceutically acceptable derivative thereof, contained within packaging material, which is used for treatment, or amelioration of one or more symptoms associated with inflammation, autoimmune disease or abnormal cell proliferation, and a label that indicates that the compound or pharmaceutically acceptable derivative thereof is used for treatment, or amelioration of one or more symptoms associated with inflammation, autoimmune disease or abnormal cell proliferation.

11. An article of manufacture, comprising packaging material, the compound of claim 8, or a pharmaceutically acceptable derivative thereof, contained within packaging material, which is used for treatment, or amelioration of one or more symptoms associated with inflammation, autoimmune disease or abnormal cell proliferation, and a label that indicates that the compound or pharmaceutically acceptable derivative thereof is used for treatment, or amelioration of one or more symptoms associated with inflammation, autoimmune disease or abnormal cell proliferation.

12. A method for preparation of a compound of the general formula 1:

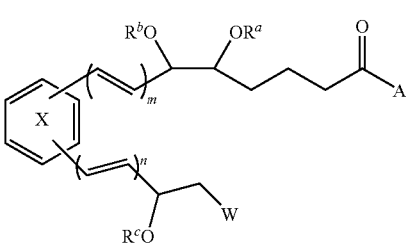

by providing a compound of formula 20, a compound of formula 21, and a compound of formula 22

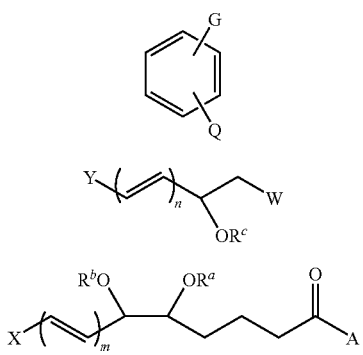

wherein:
G, Q, X and Y are independently selected from a group consisting of bromo, chloro, iodo, triflyl, diazonium, iodonium, boronic acid, boronate, borinate, borate, trifluoroborate, stannyl, perfluorostannyl, silyl, zinc, magnesium or copper;

A is hydroxy, alkoxy, aryloxy, amino, alkylamino, dialkylamino or —OM, where M is a cation selected from the group consisting of ammonium, tetra-alkyl ammonium, and the cations of sodium, potassium, magnesium and zinc;

W is hydrogen, alkyl, alkenyl, alkynyl, aryl, heteroaryl, halo, hydroxy, alkoxy, aryloxy, carboxy, amino, alkylamino, dialkylamino, acylamino, carboxamido, or sulfonamide;

$R^a$-$R^c$ are independently selected from a group costing of hydrogen, alkyl, aryl, acyl or alkoxyacyl;

the integer n is zero, one or two;

the integer m is one or two;

the two substituents on ring X are either ortho-, meta- or paraand by:
reacting a compound of formula 20, with a compound of formula 21 in the presence of a metal catalyst, followed by reaction with a compound of formula 22 in the presence of a metal catalyst selected from a group consisting of palladium, nickel and copper;

or reacting a compound of formula 20, with a compound of formula 22 in the presence of a metal catalyst, followed by reaction with a compound of formula 21 in the presence of a metal catalyst selected from a group consisting of palladium, nickel and copper.

13. The method of claim 12, where the two coupling steps are carried out in sequence or in one pot.

14. The method of claim 12, wherein 20, 21 or 22 is connected to a polymeric chain or other solid phase material.

15. A method of treating inflammation, the method comprising administering to a subject a therapeutically effective amount of a compound according to claim 1.

16. The method of claim 15, wherein the inflammation is associated with a disease or condition associated with inflammation, autoimmune diseases or abnormal cell proliferation.

17. The method of claim 16, wherein the disease is selected from rheumatoid arthritis and other forms of arthritis, asthma, psoriasis, inflammatory bowel disease, systemic lupus erythematosus, systemic dermatomyositis, inflammatory ophthalmic diseases, autoimmune hematologic disorders, multiple sclerosis, vasculitis, idiopathic nephrotic syndrome, transplant rejection and graft versus host disease.

18. The method of claim 16, wherein the abnormal cell proliferation is a non-small cell lung cancer, head and neck squamous cancers, colorectal cancer, prostate cancer, breast cancer, acute lymphocytic leukemia, adult acute myeloid leukemia, adult non-Hodgkin's lymphoma, brain tumors, cervical cancers, childhood cancers, childhood sarcoma, chronic lymphocytic leukemia, chronic myeloid leukemia, esophageal cancer, hairy cell leukemia, kidney cancer, liver cancer, multiple myeloma, neuroblastoma, oral cancer, pancreatic cancer, primary central nervous system lymphoma, skin cancer, and small-cell lung cancer.

19. A method of treating inflammation, the method comprising administering to a subject a therapeutically effective amount of a compound according to claim 8.

20. The method of claim 19, wherein the inflammation is associated with a disease or condition associated with inflammation, autoimmune diseases or abnormal cell proliferation.

21. The method of claim 20, wherein the disease is selected from rheumatoid arthritis and other forms of arthritis, asthma, psoriasis, inflammatory bowel disease, systemic lupus erythematosus, systemic dermatomyositis, inflammatory ophthalmic diseases, autoimmune hematologic disorders, multiple sclerosis, vasculitis, idiopathic nephrotic syndrome, transplant rejection and graft versus host disease.

22. The method of claim 20, wherein the abnormal cell proliferation is a non-small cell lung cancer, head and neck squamous cancers, colorectal cancer, prostate cancer, breast cancer, acute lymphocytic leukemia, adult acute myeloid leukemia, adult non-Hodgkin's lymphoma, brain tumors, cervical cancers, childhood cancers, childhood sarcoma, chronic lymphocytic leukemia, chronic myeloid leukemia, esophageal cancer, hairy cell leukemia, kidney cancer, liver cancer, multiple myeloma, neuroblastoma, oral cancer, pancreatic cancer, primary central nervous system lymphoma, skin cancer, and small-cell lung cancer.

* * * * *

UNITED STATES PATENT AND TRADEMARK OFFICE
CERTIFICATE OF CORRECTION

| | |
|---|---|
| PATENT NO. | : 8,115,023 B2 |
| APPLICATION NO. | : 12/711051 |
| DATED | : February 14, 2012 |
| INVENTOR(S) | : Nicos A. Petasis |

It is certified that error appears in the above-identified patent and that said Letters Patent is hereby corrected as shown below:

First Page, Column 2 (Other Publications), Line 15, please delete ""Dimished" and insert --"Diminished--, therefor;

First Page, Column 2 (Other Publications), Line 15, please delete "Biosysthesis" and insert --Biosynthesis--, therefor;

First Page, Column 2 (Other Publications), Line 29, please delete "aspririn" and insert --aspirin--, therefor;

First Page, Column 2 (Other Publications), Line 51, please delete "Matabolic" and insert --Metabolic--, thereof;

First Page, Column 2 (Abstract), Line 1, please delete "Benzolipoxin" and insert --Benzo lipoxin--, therefor;

Column 37, Line 62 (Claim 1), please delete "costing" and insert --consisting--, therefor;

Column 38, Line 46 (Claim 6), please delete "costing" and insert --consisting--, therefor;

Column 39, Line 31 (Claim 7), please delete "costing" and insert --consisting--, therefor;

Column 42, Lines 22-23 (Claim 17), please delete "syndrome, transplant" and insert --syndrome, and transplant--, therefor;

Column 42, line 24 (Claim 18), please delete "and small-cell" and insert --or small-cell--, therefor;

Column 42, lines 36-37 (Claim 21), please delete "syndrome, transplant" and insert --syndrome, and transplant--, therefor;

Signed and Sealed this
Thirtieth Day of October, 2012

David J. Kappos
*Director of the United States Patent and Trademark Office*

CERTIFICATE OF CORRECTION (continued)
U.S. Pat. No. 8,115,023 B2

Column 42, line 48 (Claim 22), please delete "and small-cell" and insert --or small-cell--, therefor.